(12) United States Patent
Wolschendorf et al.

(10) Patent No.: US 10,675,182 B2
(45) Date of Patent: Jun. 9, 2020

(54) HOLLOW NEEDLE FOR AN OPHTHALMIC SURGICAL INSTRUMENT

(71) Applicant: Geuder AG, Heidelberg (DE)

(72) Inventors: Marc Wolschendorf, Schriesheim (DE); Stefan Engel, Heidelberg (DE); Dieter Frauenfeld, Heidelberg (DE); René Draheim, Sandhausen (DE); Volker Geuder, Heidelberg (DE)

(73) Assignee: Geuder AG, Heidelberg (DE)

( * ) Notice: Subject to any disclaimer, the term of this patent is extended or adjusted under 35 U.S.C. 154(b) by 92 days.

(21) Appl. No.: 15/568,170

(22) PCT Filed: Feb. 2, 2016

(86) PCT No.: PCT/DE2016/200063
§ 371 (c)(1),
(2) Date: Oct. 20, 2017

(87) PCT Pub. No.: WO2016/169556
PCT Pub. Date: Oct. 27, 2016

(65) Prior Publication Data
US 2018/0110649 A1  Apr. 26, 2018

(30) Foreign Application Priority Data

Apr. 20, 2015  (DE) .................. 10 2015 207 150

(51) Int. Cl.
*A61F 9/007*  (2006.01)
(52) U.S. Cl.
CPC .... *A61F 9/00745* (2013.01); *A61B 2217/005* (2013.01)

(58) Field of Classification Search
CPC ............. A61F 9/00736; A61F 9/00745; A61B 17/320068; A61B 2017/32007
See application file for complete search history.

(56) References Cited

U.S. PATENT DOCUMENTS

| 6,074,396 A | 6/2000 | Geuder |
| 2009/0099536 A1 | 4/2009 | Akahoshi |

(Continued)

FOREIGN PATENT DOCUMENTS

| DE | 19628252 A1 | 1/1998 |
| DE | 19646881 C1 | 8/1998 |

(Continued)

OTHER PUBLICATIONS

International Search Report for PCT/DE2016/200063 dated Sep. 5, 2016.

*Primary Examiner* — Ashley L Fishback
(74) *Attorney, Agent, or Firm* — McDonnell Boehnen Hulbert & Berghoff LLP

(57) ABSTRACT

A hollow needle for an ophthalmic surgical instrument for in-vivo fragmentation of organic lenses by means of ultrasound, comprising a connection region (2) formed on the proximal end (1) for coupling onto the instrument and a needle head (4) formed on the distal end (3) having an effective surface (5) for emitting ultrasound waves, wherein a suction channel (6) for suctioning lens fragments extends in the axial direction through the hollow needle, the opening (7) of which is delimited by the effective surface (5), characterized in that the suction channel in the needle head (4) is formed in a conical manner at least partially running in the direction of the proximal end (1), and in that sections (9) running over this region (1) in the axial direction are formed in the wall (10) of the suction channel.

12 Claims, 9 Drawing Sheets

(56) References Cited

U.S. PATENT DOCUMENTS

Figure 4:
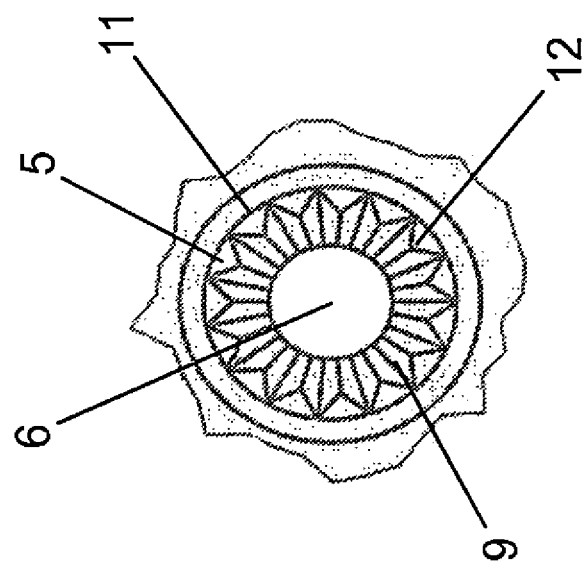

2012/0197215 A1  8/2012  Akahoshi
2014/0243842 A1  8/2014  Morlet

FOREIGN PATENT DOCUMENTS

| EP | 2737884 A1 | 6/2014 |
|---|---|---|
| JP | 03078522 U1 | 8/1991 |
| JP | 2009095662 A | 5/2009 |
| JP | 2009240622 | 10/2009 |
| JP | 2015003266 | 1/2015 |

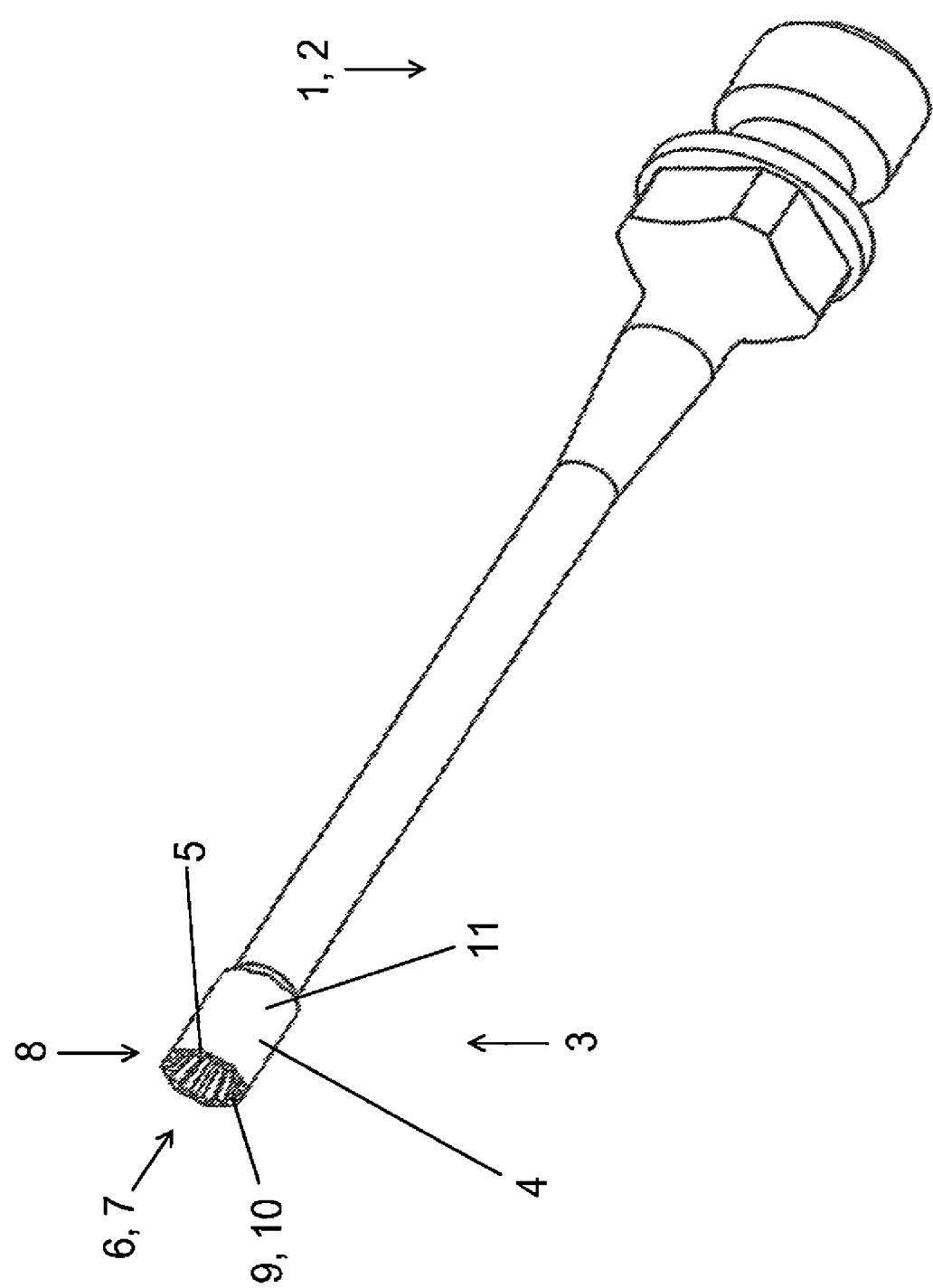

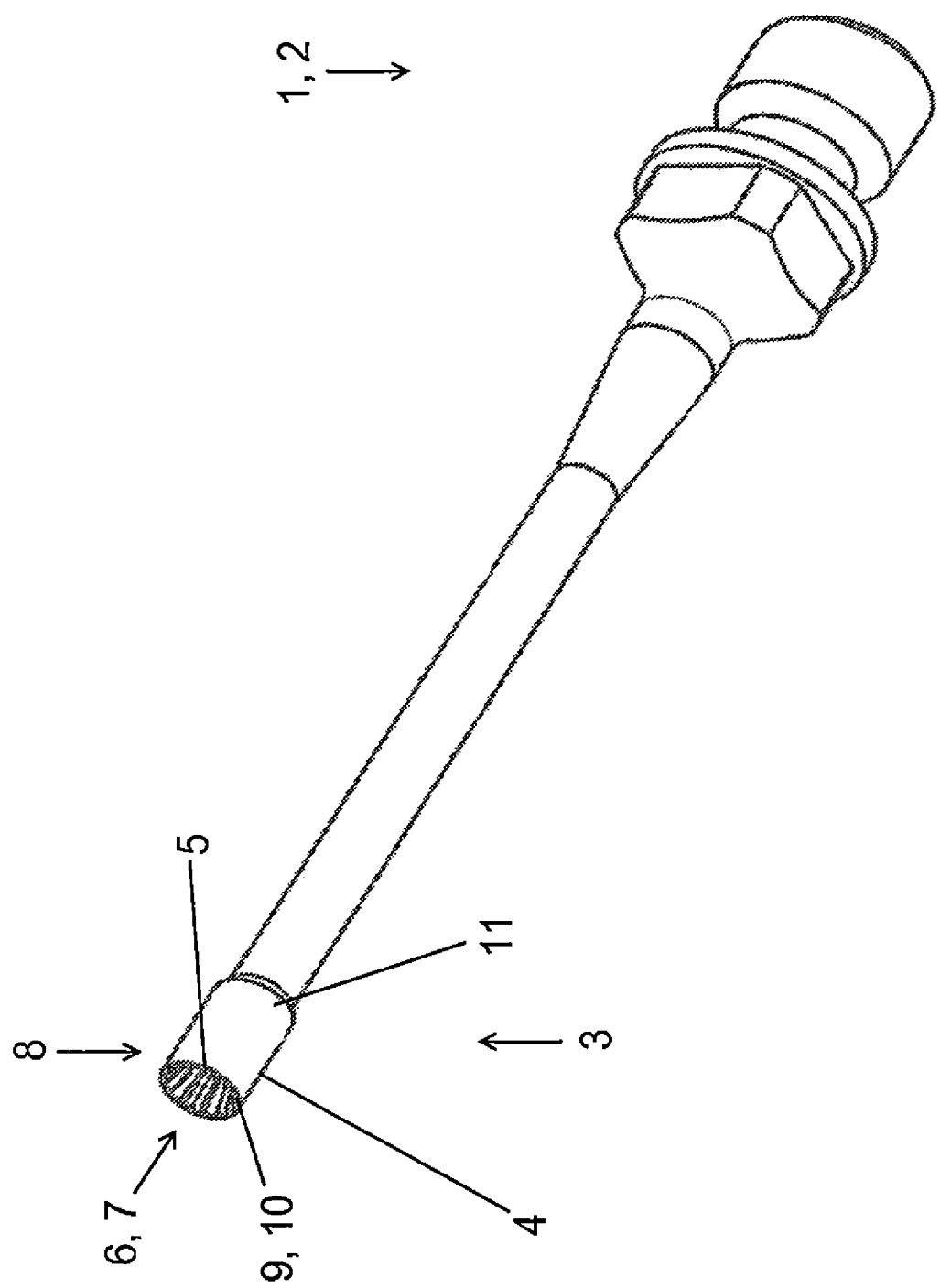

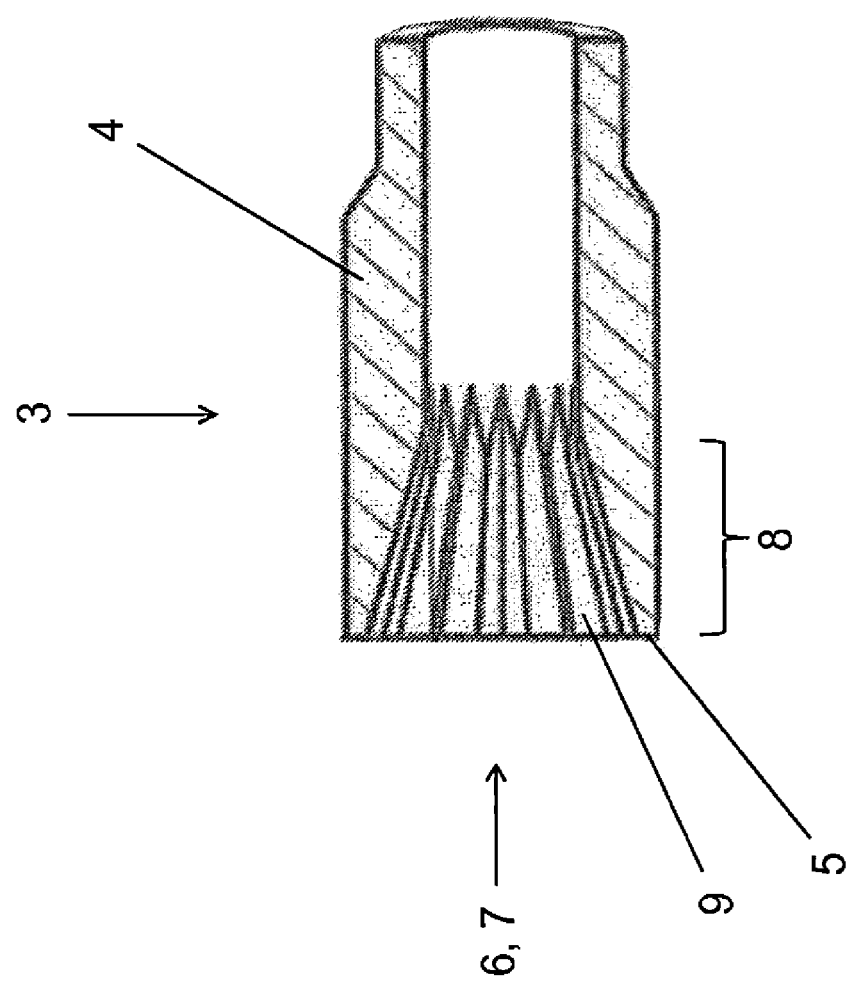

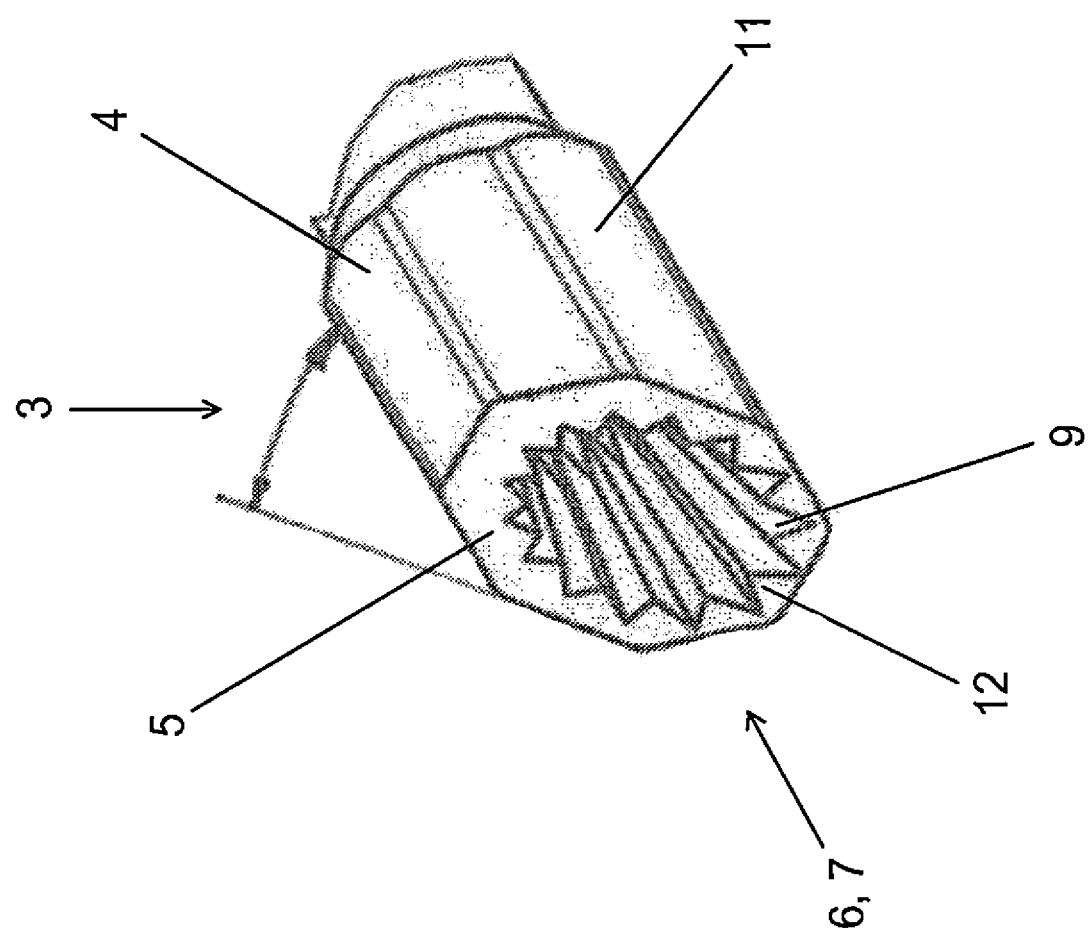

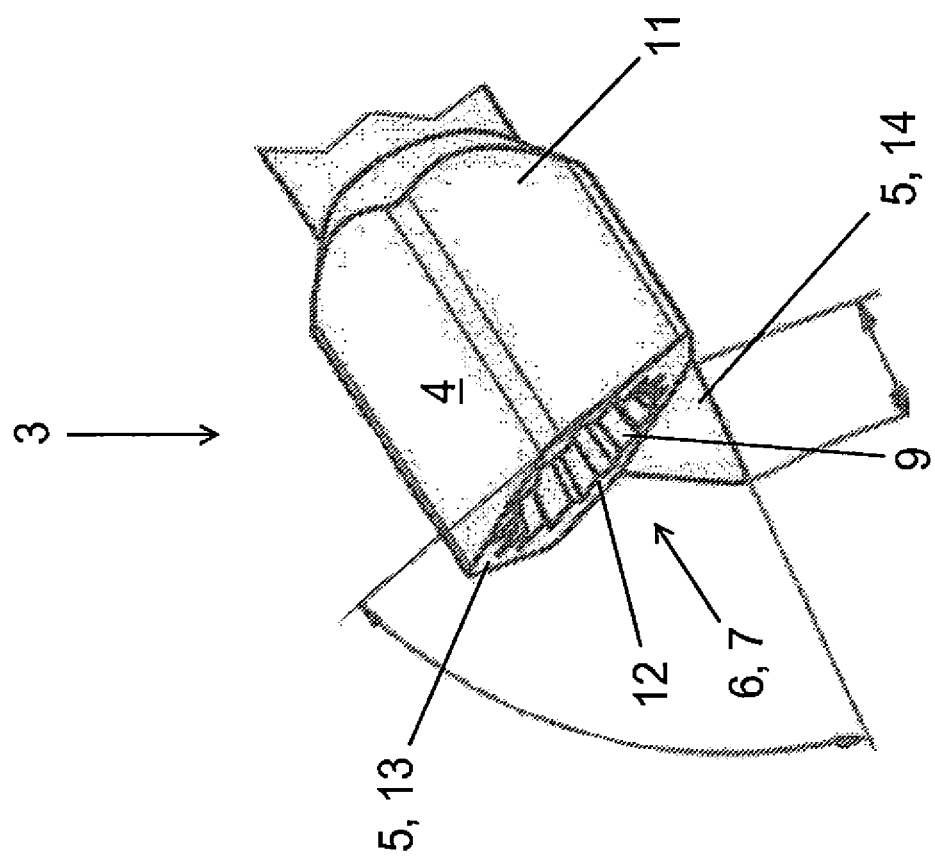

HOLLOW NEEDLE FOR AN OPHTHALMIC SURGICAL INSTRUMENT

This application is a U.S. National Phase Application pursuant to 35 U.S.C. § 371 of International Application No. PCT/DE2016/200063 filed Feb. 2, 2016, which claims priority to German Patent Application No. 10 2015 207 150.2 filed Apr. 20, 2015. The entire disclosure contents of these applications are herewith incorporated by reference into the present application.

The invention relates to a hollow needle for an ophthalmic surgical instrument for in-vivo fragmentation of organic lenses by means of ultrasound, comprising a connection region formed on the proximal end for coupling onto the instrument and a needle head formed on the distal end having an effective surface for emitting ultrasound waves, wherein a suction channel for suctioning lens fragments extends in the axial direction through the hollow needle, the opening of which is delimited by the effective surface.

Hollow needles of the type mentioned above have been well-known in practice for many years. Such a hollow needle was disclosed in U.S. Pat. No. 6,074,396 A. The suction channel within the needle head is designed in a graded manner, wherein at least some of these steps have prism-shaped sections, to improve the fragmentation of the lens body.

Furthermore, DE 196 46 881 C1 shows a hollow needle to be used in ophthalmology. This specific case involves a hollow needle for an ophthalmic surgical instrument for in-vivo fragmentation of lenses by means of high-frequency operation of the hollow needle, wherein the hollow needle is also used for simultaneously suctioning lenses through an internal suction channel. The hollow needle comprises a circular end face, which forms the opening of the suction channel.

Ultrasound operated hollow needles of the generic type are used for cataract operations in ophthalmic surgery. The free end of the hollow needle is moved into a high frequency motion and is directly brought up to the cataract. Ultrasound waves are emitted from the circular end face to emulsify the tissue. Separated lens portions or lens debris are discharged through the hollow needle, together with a cleaning liquid, which is applied to the eye.

To strengthen the emitted ultrasound field, it has already been known to provide the frontal or distal end of the hollow needle, i.e., the effective surface there, with a serrated design. As a result, the effective surface used for emitting the ultrasound waves is extended, thus improving the efficiency of the instrument or the hollow needle.

However, in practice, the well-known hollow needles involve some difficulties, because the fragmentation of the lenses takes place very slowly. To keep the stress level for the patient, which results from the surgical procedure, as low as possible, efforts are made to minimize the duration of surgery. A further difficulty involves the fact that sometimes larger lens debris are suctioned out with the generic hollow needle, which then block the suction channel and are crushed in said channel at an extremely slow pace.

Therefore, the present invention is based on the objective of designing and further developing a hollow needle for an ophthalmic surgical instrument of the generic type in such a way that an effective fragmentation of organic lenses can be performed with constructively simple means in a short period of time.

According to the invention, the above-mentioned problem is solved by the characteristics of Claim 1. Accordingly, the hollow needle of the type mentioned above for an ophthalmic surgical instrument for in-vivo fragmentation of organic lenses is characterized in that the suction channel in the needle head is formed in a conical manner at least partially running in the direction of the proximal end, and in that sections running over this region in the axial direction are formed in the wall of the suction channel.

In an inventive manner, it was first of all recognized that the basic problem could be solved through a clever geometric configuration of the suction channel in the needle head. For this purpose, the suction channel in the needle head is formed in a conical manner at least partially running in the direction of the proximal end, thus reducing the diameter of the suction channel in the needle head in the direction of the proximal end. As a result, no radially running steps or edges exist within the suction channel, on which steps or edges lens debris get stuck and block the suction channel. In addition, it has been recognized in an inventive manner that the fragmentation of the lenses can be improved in an amazingly simple way in that the wall of the suction channel comprises sections running in the axial direction over the entire conically shaped region. This simple constructive measure optimizes the emission of the ultrasound waves, thus allowing for an improved fragmentation of organic lenses. At the same time, the conical design of the suction channel and the sections arranged in the conical region provide a combinational effect, which results in an especially quick and secure fragmentation of the lens tissue.

Advantageously, recesses, especially in tetrahedral form, can be formed directly at the distal end of the needle head in the wall of the suction channel. In circumferential direction, these recesses can be arranged, for example, in radially symmetrical manner. In this region, the diameter of the suction channel can be also extended. This design has the advantage that directly at the distal end of the hollow needle the emission of the ultrasound waves is maximized, which improves the efficiency of the fragmentation.

In a specific case the sections can have a polygonal cross section. For example, the sections can have a triangular cross section, which means they can be easily produced. By this constructive measure, a tooth-like structure is implemented between the sections in the wall of the suction channel, which is useful for fragmenting especially hard lens portions.

Depending on the toughness of the lens to be fragmented, the sections can be arranged in circumferential direction in radially symmetrical or asymmetrical manner.

In an advantageous manner, the conical region can extend through a part of the hollow needle head. Furthermore, it is possible that the conical region extends through the entire needle head, so that the maximum surface is implemented for emitting ultrasound waves.

In a further advantageous manner, the conical region can start directly at the distal end of the hollow needle, so that a maximum of ultrasound waves is applied to the suctioned lens debris already at the beginning of the suction channel. If recesses are provided at the distal end of the suction channel, the conical region can start directly behind the recesses. Furthermore, it is possible that the conical region starts offset from the distal end, i.e., in the direction of the proximal end. Such a construction is suitable for an especially gentle fragmentation of the lens.

To further increase the so-called "jack hammer portion", i.e., the efficiency of the hollow needle, the sections can run in the direction of the proximal end, beyond the conical region. Furthermore, to increase this effect, it is possible to form the external wall of the needle head in polygonal manner, for example, in rectangular, pentagonal, hexagonal or octagonal manner. To protect the tissue surrounding the lens to be fragmented, the external wall of the needle head can also have a round design.

To extend the effective surface, said surface can run diagonally to the axial direction. Furthermore, it is possible that the effective surface runs perpendicular to the axial direction, to protect the surrounding tissue against injuries.

In an especially advantageous manner, the effective surface comprises two effective surface regions extending at different angles in relation to the axial direction, so that the effective surface is designed in the form of a beak. The beak-like geometry allows for an especially effective and concentrated emission of ultrasound waves, so that even tough regions of the lens to be fragmented, for example, a cataract existing already for a long period of time, are destroyed rapidly.

In a further advantageous manner, the effective surface is delimited by an external edge, wherein the external edge can have a chamfered, blunt or sharp design. A chamfered or blunt design of the edge is used to avoid injuries of the surrounding tissue. A sharp design of the external edge allows for an especially effective fragmentation of the lens.

There are different possibilities to design or further develop in an advantageous manner the technical teaching of the present invention. For this purpose, reference is made to the claims subordinate to Claim 1, as well as the subsequent description of preferred embodiments of the invention by means of the drawing. In the context of explaining the preferred embodiments of the invention by means of the drawing, also generally preferred embodiments and further developments of the technical teaching are discussed. The drawing shows FIG. 1 a schematic view of a first embodiment of an inventive hollow needle, FIG. 2 a schematic view of a further embodiment of an inventive hollow needle, FIG. 3 a schematic frontal view of the hollow needle shown in FIG. 1, FIG. 4 a schematic frontal view of the hollow needle shown in FIG. 2, FIG. 5 an enlarged schematic view of an embodiment of the needle head of an inventive hollow needle, FIG. 6 an enlarged schematic view of an embodiment of the needle head of the inventive hollow needle shown in FIG. 4, FIG. 7 an enlarged sectional view of a further embodiment of the needle head of an inventive hollow needle, FIG. 8 an enlarged schematic view of a further embodiment of the needle head of an inventive hollow needle, FIG. 9 an enlarged schematic view of a further embodiment of the needle head of an inventive hollow needle, FIG. 10 a schematic view of a further embodiment of the needle head of an inventive hollow needle and FIG. 11 an enlarged schematic view of a further embodiment of the needle head of an inventive hollow needle.

FIG. 1 shows a schematic view of a first embodiment of an inventive hollow needle for an ophthalmic surgical instrument for in-vivo fragmentation of organic lenses by means of ultrasound. The hollow needle comprises a connection region 2 formed on the proximal end 1 for coupling onto the instrument (not shown in the figures) and a needle head 4 formed on the distal end 3. The needle head 4 has an effective surface 5 for emitting ultrasound waves. A suction channel 6 for suctioning lens fragments extends in the axial direction through the hollow needle, the opening 7 of which is delimited by the effective surface 5. In this embodiment, the suction channel 6 runs coaxially to the symmetrical axis of the hollow needle.

The suction channel 6 in the needle head 4 is formed in a conical manner at least partially running in the direction of the proximal end. The wall 10 of the suction channel 6 comprises sections 9 running in the axial direction over the entire conically shaped region. In circumferential direction, the sections 9 are arranged in radially symmetrical manner. For better clarity, only one section 9 shown in the figures is provided with a reference numeral.

In the embodiment shown, the external wall 11 of the needle head has an octagonal design, which increases the "jack hammer portion" when fragmenting the lenses.

FIG. 2 shows a schematic view of a further embodiment of an inventive hollow needle. The embodiment shown in FIG. 2 corresponds to the embodiment shown in FIG. 1, whereas the external wall 11 of the needle head 4 shown in FIG. 2 has a round design. The hollow needle shown in FIG. 2 is suitable for an especially tissue-conserving fragmentation of lenses.

Figure 3:
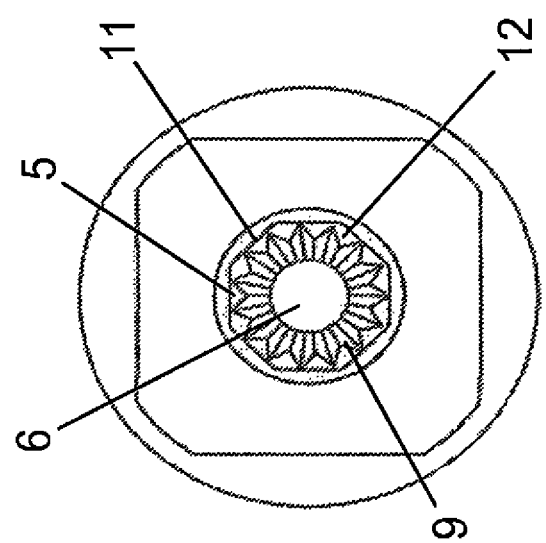

FIG. 3 shows a schematic, frontal view of the hollow needle shown in FIG. 1. It clearly shows the octagonal external wall 11 of the needle head 4. FIG. 3 also clearly shows that the suction channel 6 in the needle head 4 is formed in a conical manner running in the direction of the proximal end 1 and that it has sections 9 running in the axial direction. The suction channel 6 runs coaxially to the symmetrical axis of the hollow needle. The sections 9 comprise a triangular cross section, so that teeth 12 are implemented between the sections in the wall 10. To enhance clarity, only individual teeth 12 are provided with reference numerals in the figures.

FIG. 4 shows a schematic, frontal view of the hollow needle shown in FIG. 2. It is again clearly shown that the external wall 11 has a round design. Furthermore, the embodiment shown in FIG. 4 corresponds to the embodiments shown in FIGS. 1 and 3.

Figure 5:
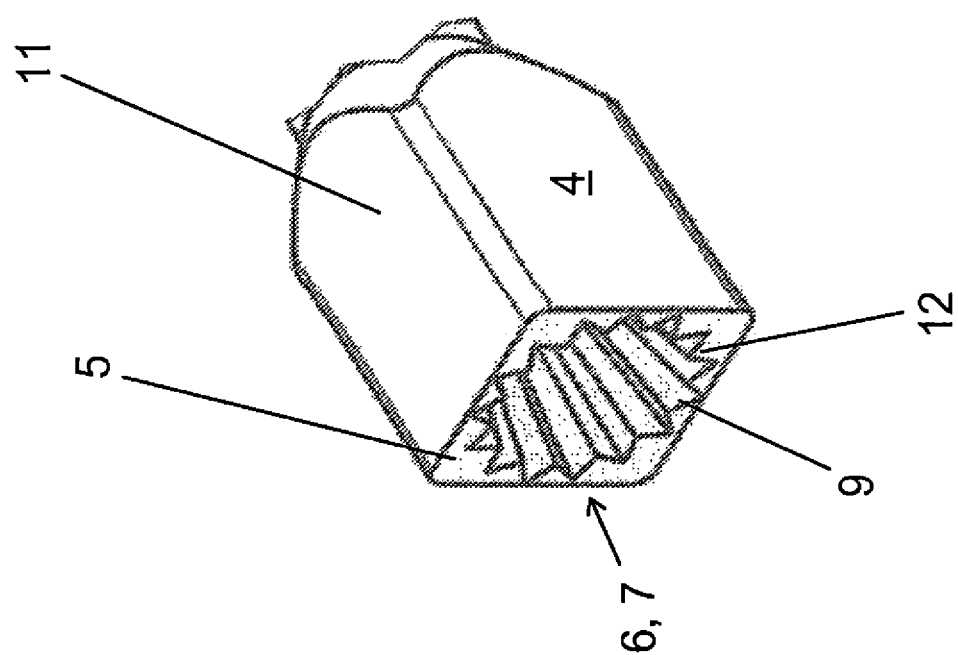

FIG. 5 shows an enlarged schematic view of an embodiment of the needle head 4 of an inventive hollow needle. Here, the external wall 11 has a rectangular design. Furthermore, FIG. 5 corresponds to the embodiment shown in FIGS. 1 and 3, so that it is not necessary to show additional embodiments.

Figure 6:
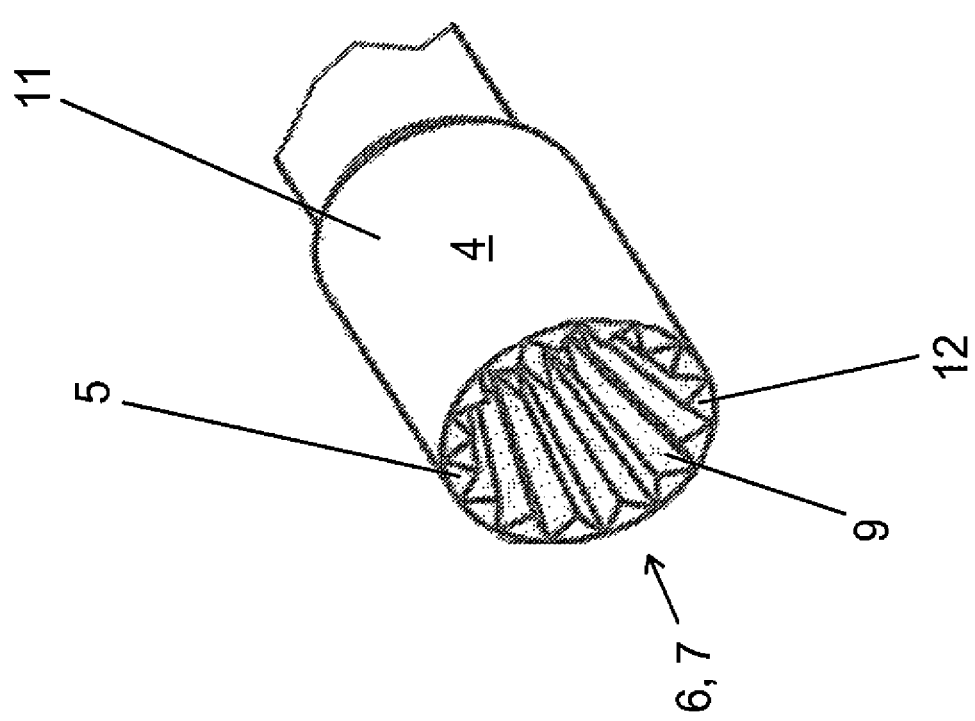

FIG. 6 shows an enlarged schematic view of the needle head 4 of the hollow needle shown in FIG. 4. In this representation, the triangular cross section of the sections 9 can be seen, by means of which the teeth 12 can be implemented.

FIG. 7 shows an enlarged sectional view of a further embodiment of the needle head 4 of an inventive hollow needle. In the embodiment shown in FIG. 7, the conical region 8 starts directly at the distal end 3 of the needle head 4. The region 8 extendsover the entire needle head. The sections 9 run in the direction of the proximal end 1 beyond the conical region 8.

FIG. 8 shows an enlarged sectional view of a further embodiment of the needle head 4 of an inventive hollow needle. The external wall 11 of the needle head 4 has an octagonal design. Furthermore, the effective surface 5 runs perpendicular to the axial direction, so that the effective surface 5 is enlarged. It is also shown that the suction channel 6 runs not in coaxial, but in parallel offset manner to the symmetrical axis of the hollow needle.

Figure 9:
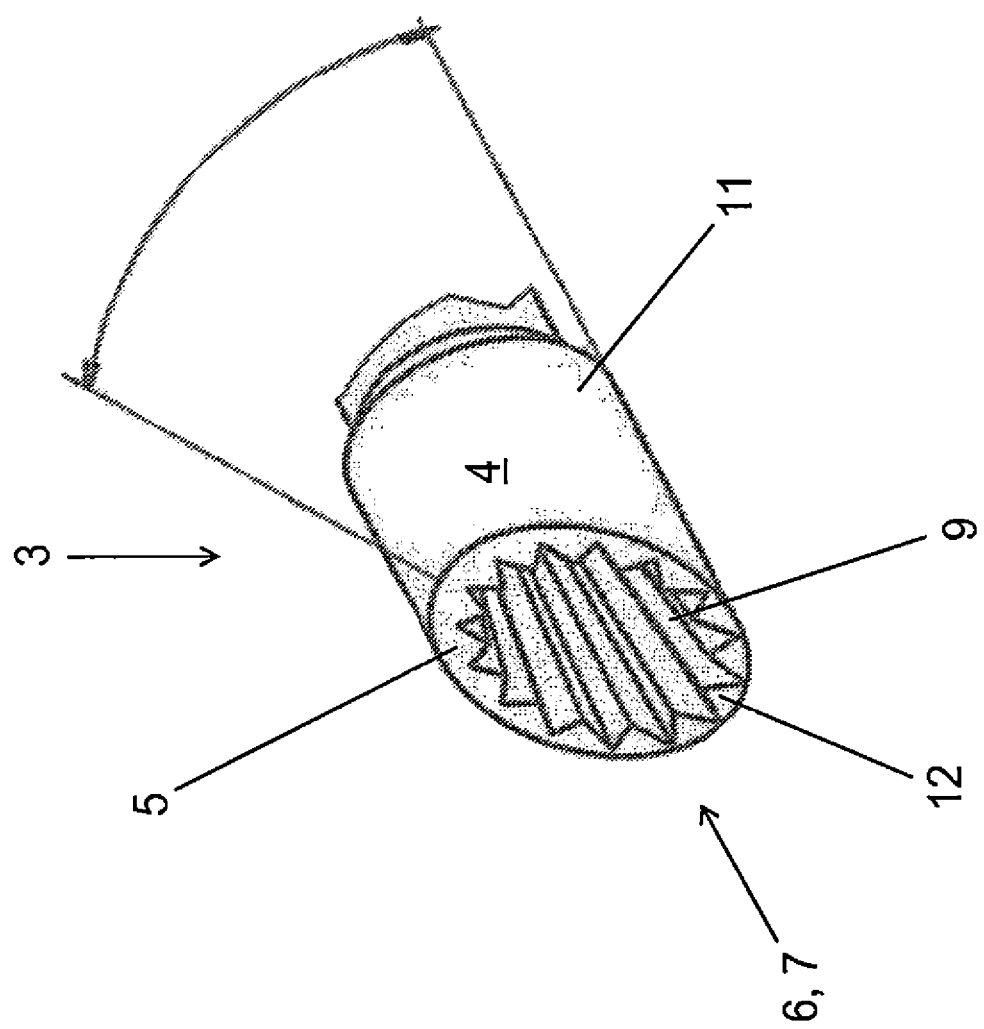

FIG. 9 shows an enlarged sectional view of a further embodiment of the needle head 4 of an inventive hollow needle. The needle head 4 has an external wall 11 which is designed in a round manner. The effective surface 5 runs perpendicular to the axial direction. Also in this case, the suction channel 6 runs not in coaxial, but in parallel offset manner to the symmetrical axis of the hollow needle.

Figure 10:
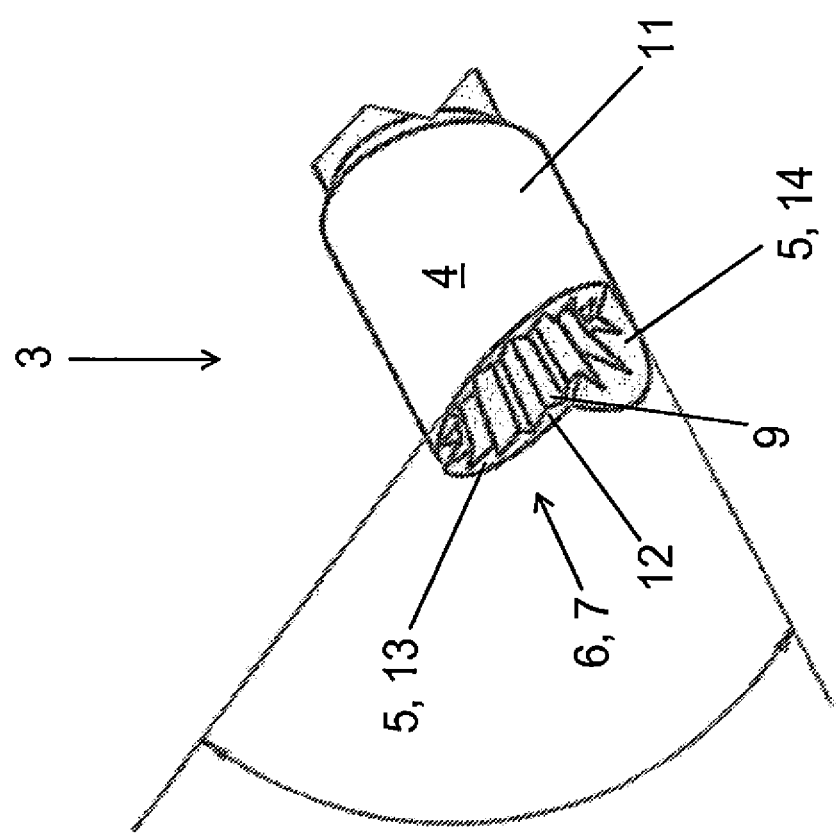

FIG. 10 shows an enlarged sectional view of a further embodiment of the needle head 4 of an inventive hollow needle. In this embodiment, the effective surface 5 of the needle head 4 comprises two effective surface regions 13, 14. The first effective surface region 13 extends at a different angle than the second effective surface region 14 in relation to the axial direction, so that the effective surface 5 is designed in the form of a beak. Such a construction comprises an especially large "jack hammer portion", which results in an effective fragmentation of the lenses. The external wall 11 has a round design. However, it is also possible to design the external wall 11 in polygonal manner, for example, in rectangular or octagonal manner.

FIG. 11 shows an enlarged sectional view of a further embodiment of the needle head 4 of an inventive hollow needle. In this embodiment, the effective surface 5 of the needle head 4 comprises two effective surface regions 13, 14. The first effective surface region 13 extends at a different angle than the second effective surface region 14 in relation to the axial direction, so that the effective surface 5 is designed in the form of a beak. FIG. 11 also shows that the second effective surface region 14 is arranged in the radial direction so far to the outside that the suction channel 6 does not extend all the way up to the second effective surface region 14.

To avoid repetitions, reference is made to the general part of the description, as well as to the attached claims with regard to further advantageous embodiments of the inventive device.

In conclusion, it should be emphasized that the embodiments of the inventive device described above only have the purpose of discussing the technical teaching claimed, but do not limit said teaching to these embodiments.

LIST OF REFERENCE NUMERALS 1 proximal end
2 Connection region
3 distal end
4 needle head
5 effective surface
6 suction channel
7 opening
8 conical region
9 section
10 wall (suction channel)
11 external wall

The invention claimed is:

1. A hollow needle for an ophthalmic surgical instrument for in-vivo fragmentation of organic lenses by means of ultrasound, comprising a connection region (2) formed on a proximal end (1) for coupling onto the instrument and a needle head (4) formed on a distal end (3) having an effective surface (5) for emitting ultrasound waves, wherein a suction channel (6) for suctioning lens fragments extends in an axial direction through the hollow needle, an opening (7) of which is delimited by the effective surface (5), wherein the suction channel in the needle head (4) is formed in a conical manner at least partially running in the direction of the proximal end (1), wherein sections (9) running over this region (1) in the axial direction are formed in a wall (10) of the suction channel, and wherein the effective surface (5) comprises two effective surface regions (13, 14) extending at different angles in relation to the axial direction, such that the effective surface (5) is designed in the form of a beak.

2. The hollow needle according to claim 1, characterized in that directly at the distal end of the needle head (4) in the wall (10) of the suction channel (6) recesses are formed.

3. The hollow needle according to claim 1, characterized in that the sections (9) have a polygonal cross section.

4. The hollow needle according to claim 1, characterized in that the sections (9) are arranged in a circumferential direction in a radially symmetrical or asymmetrical manner.

5. The hollow needle according to claim 1, characterized in that a conical region (8) extends through a part of the hollow needle head (4) or through the entire needle head (4).

6. The hollow needle according to claim 1, characterized in that a conical region (8) starts directly at the distal end (3) or offset from the distal end (3), in the direction of the proximal end (1).

7. The hollow needle according to claim 1, characterized in that the sections (9) run in the direction of the proximal end (1), beyond the conical region (8).

8. The hollow needle according to claim 1, characterized in that an external wall (11) of the needle head (4) is designed in a round or polygonal, for example, rectangular, pentagonal, hexagonal or octagonal manner.

9. The hollow needle according to claim 1, characterized in that the effective surface (5) extends perpendicular or diagonally to the axial direction.

10. The hollow needle according to claim 1, characterized in that effective surface (5) is delimited by an external edge, wherein the external edge can have a chamfered, blunt or sharp design.

11. The hollow needle according to claim 1, characterized in that directly at the distal end of the needle head (4) in the wall (10) of the suction channel (6) recesses in tetrahedral form are formed.

12. The hollow needle according to claim 1, characterized in that the sections (9) have a triangular cross section.

* * * * *